United States Patent [19]

Patton et al.

[11] Patent Number: 4,834,094
[45] Date of Patent: May 30, 1989

[54] "CANOE" APPARATUS FOR INSERTING INTRA-OCULAR LENS INTO THE EYE

[75] Inventors: Douglas M. Patton, Irvine; Matthew F. Duncan, Mission Viejo, both of Calif.

[73] Assignee: Patton Medical Technologies, Inc., Costa Mesa, Calif.

[21] Appl. No.: 172,374

[22] Filed: Mar. 24, 1988

Related U.S. Application Data

[63] Continuation-in-part of Ser. No. 106,044, Oct. 7, 1987.

[51] Int. Cl.$^4$ .............................................. A61B 17/00
[52] U.S. Cl. ..................................... 128/303 R; 623/6
[58] Field of Search ........................ 128/303 R; 623/6

[56] References Cited

U.S. PATENT DOCUMENTS

| 4,681,102 | 7/1987 | Bartell | 128/303 R |
| 4,702,244 | 10/1987 | Mazzocco | 128/303 R |
| 4,715,373 | 12/1987 | Mazzocco et al. | 128/303 R |

Primary Examiner—Michael H. Thaler
Attorney, Agent, or Firm—Lyon & Lyon

[57] ABSTRACT

There is disclosed herein an apparatus and method for curling and confining a flexible lens and for inserting and injecting the same into the eye. The apparatus includes an insertion cartridge including an insertion tip having a lens holder in the form of a "canoe," a constricting sleeve for causing the lens to curl within the tip, and a plunger for moving the lens out of the tip and injecting the same into the eye. The injection tip is configured in a particular manner to enable the lens to uncurl gently and thereby be gently inserted into the eye. There also is disclosed a hand held instrument for holding and manipulating the lens insertion cartridge, and a control unit and control system for controlling advancement of the lens out of the lens cartridge. Also disclosed is a lens cartridge loader which allows a physician to load an intra-ocular lens into the lens cartridge in a simple, one handed operation.

6 Claims, 6 Drawing Sheets fig. 1.

"CANOE" APPARATUS FOR INSERTING INTRA-OCULAR LENS INTO THE EYE

CROSS-REFERENCE TO RELATED APPLICATIONS

The present application is a continuation-in-part of U.S. patent application Ser. No. 07/106,044 filed Oct 7, 1987 entitled "APPARATUS FOR INSERTING ARTIFICIAL INTRA-OCULAR LENSES INTO HUMAN EYES FOR LENS IMPLANTING," and assigned to the assignee of the present invention. The present application also is related in subject matter to U.S. patent application Ser. No. 172,371 filed concurrently herewith in the names of the present inventors entitled "ENVELOPE APPARATUS AND METHOD FOR INSERTING INTRA-OCULAR LENS INTO THE EYE" and assigned to the assignee of the present invention. The disclosures of the above applications are incorporated herein by reference.

BACKGROUND OF THE INVENTION

1. Field of the Invention

The present invention relates generally to the field of apparatus and methods for surgically implanting artificial lenses in the human eye, and particularly to the implanting of artificial intra-ocular lenses in cataract surgery in place of diseased or damaged natural intra-ocular lenses as part of the lens implanting operation.

2. Discussion of the Background

Vision is the ability of the eye to form an image of an object and send the image to visual centers of the brain. In this process, light rays from the object pass through the cornea, the aqueous humor, the pupil, the intra-ocular lens (IOL) and the vitreous humor of the eye. These rays finally reach the retina where they stimulate the optic nerve cells. In turn, the optic nerve carries "messages" from the nerve cells to the visual cortex of the brain. The disc-shaped intra-ocular lens in the eye performs the same function as the lens of a camera and is responsible for focusing incoming light rays onto the retina, which is the image registering portion of the eye.

Injury and disease can affect the ability of an intra-ocular lens to perform its function of focusing and transmitting light rays. In particular, a cataract is a lessening of the transparency of the lens when the normally clear fibers, which comprise the lens, become cloudy. As a consequence, adequate light cannot reach the associated retina, and vision becomes increasingly blurred. Cataracts tend to be relatively common in persons over about 65 or 70 years of age; however, in younger persons a cataract may be present at birth or may result at any age from injury or disease. Diabetes can, for instance, cause cataracts to occur, as can glaucoma.

So far, as is known, there presently exists no treatments or medicines which can reverse a cataract and cause the cloudy lens fibers to become clear and transparent again. The only effective treatment for a cataract is surgical removal of the affected lens, and, until relatively recently, optical compensation for a removed lens was limited to strong glasses which were clumsy and heavy or contact lenses, although the latter are frequently incapable of providing sufficient focusing effect.

Medical technology has, however, recently advanced to the state that a diseased or damaged intra-ocular lens can now be replaced by an artificial intra-ocular lens which is surgically implanted in the eye behind the cornea after the natural lens has been removed. These artificial lenses can, like regular glasses or contact lenses, be specially made to correct other eye deficiencies and are, for example, commonly available in a variety of diopters. A typical medical protocol followed in replacing a diseased or damaged, natural intra-ocular lens with an artificial intra-ocular lens involves first making a small surgical incision or aperture in the cornea near its edge and to one side of the iris. The diseased or damaged natural intra-ocular lens is surgically removed through this corneal aperture, by such means as ultrasonically fracturing the lens and then extracting, as by the application of suction, the lens tissue. Next, an artificial replacement lens is carefully inserted into the eye through the same corneal aperture and is manipulated by the surgeon into the same position, behind the iris, previously occupied by the removed natural lens. According to the particular configuration of the artificial lens being installed, appropriate surgical techniques are then used to secure the artificial lens in its proper position in the eye. Finally, the incision made through the cornea is repaired.

For this type of surgical lens implantation procedure, it is known to use a flexible artificial lens, constructed of a material such as silicone, and to manually bend or curl the lens, for example, by forceps, into a tubular shape before insertion so that the size of the corneal aperture needed for insertion can be made as small as possible to minimize trauma to the eye. As soon as the artificial lens, when curled into tubular form, is inserted through the corneal aperture and is released, it uncoils on its own into its original flat, disc shape. This procedure of coiling an artificial lens into tubular form permits, by way of illustration, an artificial lens having a diameter of about one quarter inch to be inserted through a corneal opening only about one tenth of an inch across. The use of the above-described type of intra-ocular lens implantation technique is disclosed, for example, in U.S. Pat. No. 4,573,998 to T. Mazzocco, the disclosure of which is incorporated herein by reference.

Small artificial intra-ocular lenses are, however, extremely difficult to manually fold or curl into a small shape by forceps or other conventional medical instruments without scratching or otherwise damaging the lens. Moreover, the eye itself is so extremely delicate that even the merest touch of the tip of a surgical instrument or of a edge of the artificial lens on the one-cell layer of the endothelial lining on the posterior face of the cornea can tear some of the cells away from the corneal surface and permanently injure the eye.

Because of the difficulty in manually curling and inserting an artificial lens through a small incision in the cornea, various lens inserting instruments or apparatus have been developed or proposed for mechanically folding a flexible artificial lens and for then inserting the lens through the corneal incision into the eye. One such type of artificial lens inserting instrument believed to have been used in surgical lens implanting resembles a hypodermic syringe, in that it has a cylindrical barrel with an internal plunger and a converging, funnel-shaped insertion tip and a flanged chamber for holding the lens. A device of this nature is disclosed in U.S. Pat. No. 4,681,102.

In using such a syringe-type instrument, an artificial intra-ocular lens to be implanted in a patient's eye is placed in the instrument barrel and folded therein. An appropriate surgical incision is made in the patient's cornea and the natural intra-ocular lens is removed in a manner such as described above. The end of the insertion tip is then inserted through the corneal incision and the plunger of the instrument is depressed so as to push against a side edge of the artificial lens in the barrel. Depressing the plunger of the instrument forces the lens out of a cylindrical tip of the instrument and into the patient's eye.

A principal disadvantage associated with such types of artificial lens inserting instruments is that the lens tends to abruptly spring out of the tip. As has been emphasized above, an eye is extremely delicate and any abrupt ejection of the replacement lens from the inserting instrument into a patient's eye can result in the lens damaging delicate eye tissue and causing eye injury.

Even if the lens itself does not cause any eye injury in such circumstances, the abrupt ejection may result in the lens being incorrectly positioned in the eye, and the additional manipulation required to correctly position and align the lens may injure the eye. Further in this regard, it is also highly desirable that the lens transplant operation be completed as rapidly as possible and the corneal incision be quickly repaired so as to minimize trauma to the eye and reduce the possibility of infection. Therefore, the lens insertion instrument used should accurately position the artificial lens as the lens is inserted into the eye, so that the amount of subsequent manipulation of the lens is kept to a minimum.

For these and other reasons related to minimizing trauma to a patient's eye during and as a result of any intra-ocular lens transplant operation, improvements are needed to lens inserting apparatus and methods. Ideally, such improved apparatus should provide the ophthalmic surgeon who performs lens transplant operations complete and precise control of lens insertion into the patient's eye and should, therefore, eliminate or at least substantially reduce any tendency of the replacement lens to abruptly spring out of the insertion instrument into the eye during the insertion process. Additionally, such improved apparatus should leave at least one of the performing surgeon's hands free to hold other instruments, manipulate the patient's eye or otherwise assist with the operation.

The inventions described in applicants' previously referenced U.S. patent applications provide significant improvements in these respects. The apparatus and method disclosed in application Ser. No. 07/106,044 provides a convenient and simple means of receiving, holding and confining an intra-ocular lens, and one which provides an injector tip configuration and controlled movement of the lens out of the instrument in a manner to reduce abrupt springing of the lens out of the tip. The invention of the application referred to above and which is filed concurrently herewith shows and describes an entirely different technique wherein the lens is held and curled in what may be termed an "envelope" fashion and in which the lens as it moves out of the tip gently flowers out to eliminate such problems. The subject matter of the present application represents an improvement and modification of the apparatus and method disclosed in U.S. patent application Ser. No. 07/106,044 in that it provides improved lens holder and injector tip configurations, and means and methods of more gently passing the lens out of the tip and into the eye.

SUMMARY OF THE INVENTION

The present invention provides a medical apparatus and method for inserting a flexible artificial intra-ocular lens into a patient's eye through a small incision therein for the replacement of a removed natural lens. While the present apparatus and method will be described specifically with respect to insertion of an intra-ocular lens, the apparatus and method of the present invention also are applicable in refractive surgery in the cornea of the eye.

The apparatus of the present invention includes three major components, namely a control unit, hand held instrument and lens insertion cartridge. The hand held instrument preferably is connected at one end to the control unit by a flexible drive cable, and the insertion cartridge is attached to the other end of the instrument. The instrument provides a convenient means whereby the physician can hold and operate the insertion cartridge with one hand, and the instrument is connected to the control unit by the flexible drive cable which provides a controlled force to advance the lens through and out of the cartridge and into the eye during the surgical procedure. The instrument and control unit, while not identical, are similar to those shown and described in said application Ser. No. 07/106,044.

The insertion cartridge comprises three components. The first is an elongated injection tip which has a thin distal tip portion for insertion into the eye, an intermediate lens holder or receiving section in the form of a "canoe," and a proximal cylindrical portion which extends into the hand held instrument. A second component is a constricting sleeve which normally is disposed around the proximal portion of the injection tip, but which can be slid forward to close the lens holder gently around the intra-ocular lens to curl the normally flat lens into an essentially round or cylindrical shape. The third component is a plunger which is driven from the control unit in a controllable manner via the flexible cable to push the intra-ocular lens out of the distal tip end of the insertion cartridge.

The shape and construction of the tip portion of the injection tip, along with the controlled advancement of the plunger in pushing the IOL, allow the IOL to progressively and gently return to its original shape as it is moved out of the tip and injected into the eye rather than to abruptly eject from the tip as occurs with same prior devices such as shown in U.S. Pat. No. 4,681,102.

In addition to the foregoing, there is disclosed (i) an alternative hand held unit which combines in one hand held unit the instrument and the driving system, and (ii) an intra-ocular lens cartridge loader for providing a simplified means of physically loading, using one hand, the intra-ocular lens into the lens holder of the insertion cartridge.

Accordingly it is a principal object of the present invention to provide an improved form of apparatus and method for inserting artificial lenses.

Another object of this invention is to provide an improved form of apparatus and method for inserting artificial intra-ocular lenses into human eyes.

A further object of the present invention is to provide a new form of lens insertion cartridge for facilitating gentle insertion of an intra-ocular lens into the eye.

Another object is to provide a lens insertion cartridge wherein the structure and configuration of the cartridge and insertion tip, and the drive means therefor, enables the lens to be gently inserted into the eye.

Another object of the present invention is to provide a new form of artificial lens insertion cartridge comprising an injection tip and constricting sleeve for enabling simple and efficient curling of the lens into the tip and for facilitating gentle and controlled movement of the thus-curled lens out of the tip and into the eye.

A further object of the present invention is to provide an intra-ocular lens cartridge loader.

BRIEF DESCRIPTION OF THE DRAWINGS

These and other objects and features of the present invention will become better understood through a consideration of the description herein taken in conjunction with the drawings in which:

FIGS. 3a-3f, 4a-4b, 5a-5b and 6a-6c are respective cross-sectional views of the lens insertion cartridge in different states of operation, with FIGS. 3b, 4b, 5b and 6b being cross-sectional views taken along like identified lines of respective FIGS. 3a, 4a, 5a and 6a; FIG. 3c is a view like FIG. 3a but rotated ninety degrees; FIG. 3e is a view of the plunger as seen in FIG. 3d (and 3a) but rotated ninety degrees.

DETAILED DESCRIPTION

The description herein will be with reference to insertion of artificial intra-ocular lenses; however, it is to be understood that the concepts of the present invention are applicable to insertion of other forms of artificial lenses into the eye such as in refractive surgery in the cornea. In this latter regard, a relatively thin lens can be inserted through use of the apparatus and methods of the present invention in a "pita pocket" formed in the stroma layer of the cornea by suitable mechanical means. In this case, the insertion tip is approximately one-half the diameter of tha shown and described herein. Accordingly, the concepts of the present invention are not to be limited to use and insertion of any particular form of lens in the eye.

Figure 1:
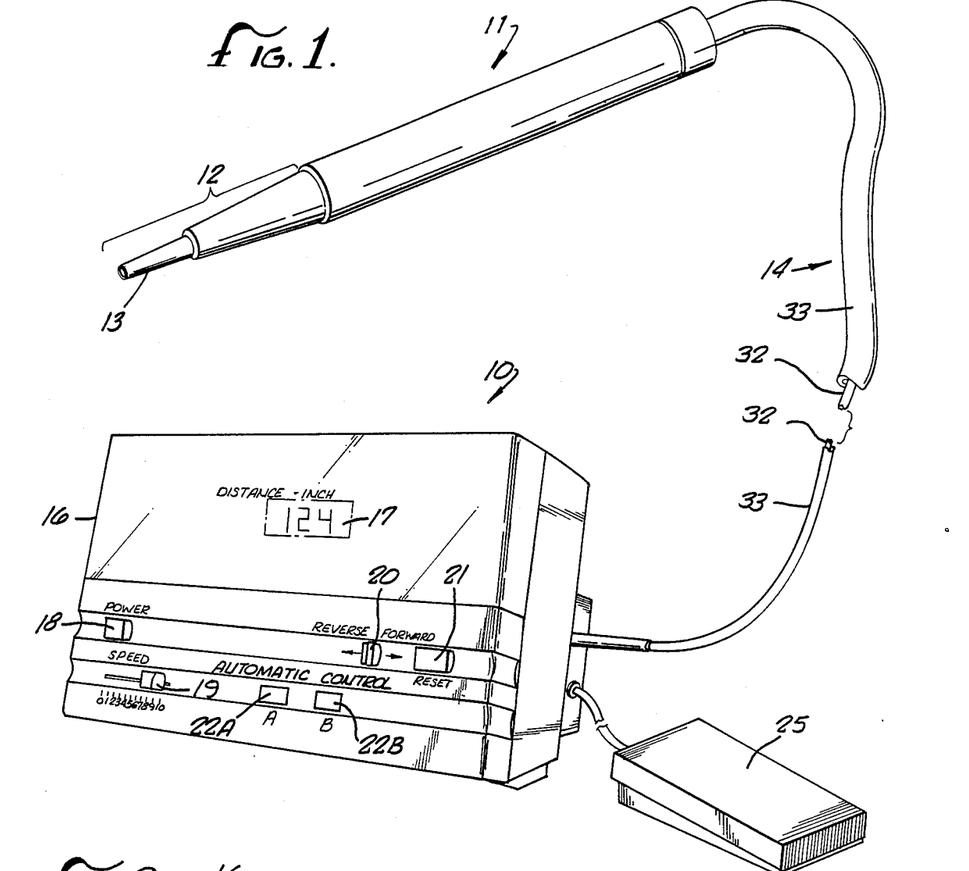
FIG. 1 is a perspective view of a control unit, hand held instrument, and lens insertion cartridge according to the present invention.

Turning now to the drawings and first to FIG. 1, the overall lens insertion system includes a control unit 10, hand held instrument or pen 11 and insertion cartridge 12. As will be explained later the insertion cartridge 12 is a disposable unit which holds an intra-ocular lens in a curled up manner such that the lens can be moved out of the tip 13 of the cartridge 12 under control of the control unit 10. The description herein will be with reference to insertion of intra-ocular lenses; however, it is to be understood that the concepts of the present invention are applicable to insertion of other forms of lenses into the eye such as in refractive surgery in the cornea. In this latter regard, a relatively thin lens can be inserted through use of the apparatus and methods of the present invention in a "pita pocket" formed in the stroma layer of the cornea by suitable mechanical means. In this case, the insertion tip is approximately one-half the diameter of that shown and described herein. Accordingly, the concepts of the present invention are not to be limited to use and insertion of any particular form of lens in the eye.

The control unit 10 includes a linear actuator or stepper motor (shown in greater detail in FIG. 2 and to be discussed subsequently) which, via a suitable flexible cable assembly 14, gently pushes the intra-ocular lens out of the tip 13 at a controlled rate, such as in one thousandth inch increments and at selectable speeds.

Figure 11:
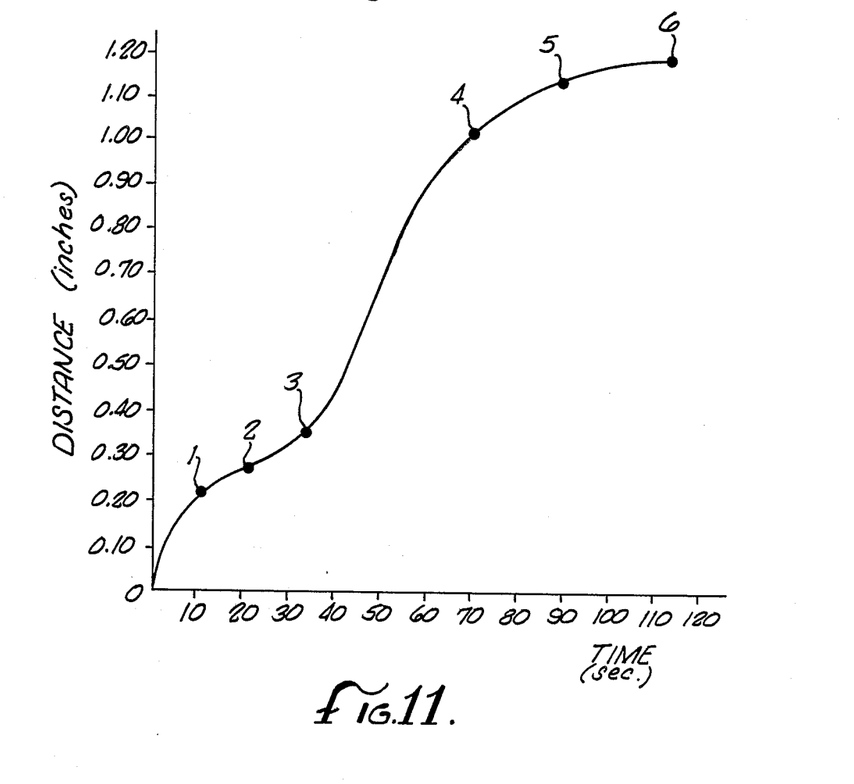
FIG. 11 is a curve illustrating a preferred form of advancement or movement rate of the lens through and from the injection cartridge during insertion into the eye as provided by the linear actuator under control of the control unit.

The control unit 10 includes a housing 16 on which is provided a visual display 17 for indicating the distance travelled by the lens in one thousandth inch increments during the insertion procedure. Also provided is a power on/off switch 18, a speed control potentiometer 19, a forward/reverse direction switch 20, a reset button 21, and automatic control buttons 22a and 22b. A foot switch 25 is connected to the control unit to allow the physician to control the advancement of the intra-ocular lens. The speed control potentiometer controls the speed of advancement when the foot pedal 25 is depressed. The direction switch 20 selects the direction of advancement or retraction of the driving cable which pushes (but does not pull) the intra-ocular lens. The reset button 21 allows the display 17 to be reset to zero. The automatic control buttons 22a-22b allow an internally programmed rate of advancement to be selected (such as is illustrated by the curve of FIG. 11 and which will be discussed later).

Figure 2:
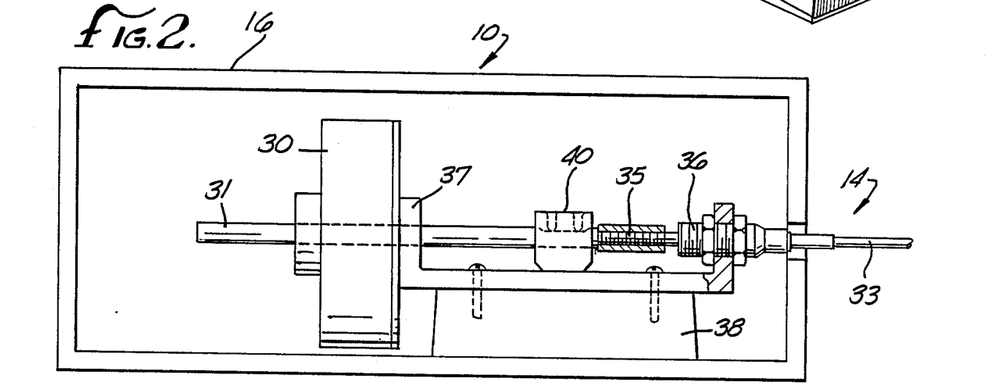
FIG. 2 is an elevational cross-sectional view of a stepper motor drive used in the control unit and for pushing an intra-ocular lens from the insertion cartridge into the eye.

FIG. 2 illustrates the stepper motor linear actuator system disposed within the control unit 10 and which is connected to the flexible cable assembly 14. This unit includes a conventional stepper motor linear actuator 30 which drives a shaft 31 linearly (to the right and to the left as viewed in FIG. 2) to drive a cable 32 (note FIGS. 1 and 8) of the flexible push/pull cable assembly 14 through the outer sheath 33 thereof. The shaft 31 is connected to the cable via a collar 35 and the cable extends through a mounting assembly 36. The actuator 30 and assembly 36 are mounted on a suitable bracket 37 attached through a base 38 to the interior of the housing 16. A stabilizing block 40 is attached to the shaft 31 and rides on bracket 37 to help stabilize the linear movement of the shaft 31.

The foregoing generally describes the overall operation of the control unit, pen and lens injector cartridge. The discussion now will proceed to the details of the injection cartridge 12 and the pen assembly 11 particularly with reference to FIGS. 3 through 8.

Considering first FIGS. 3 through 7, the insertion cartridge comprises the three major components mentioned earlier; namely, an insertion or injector tip 50, a constricting sleeve 51, and a plunger 52. The plunger 52, as will be described in greater detail later, is pushed by the flexible cable 32 to advance, and therefore move or eject, an intra-ocular lens out of the tip 50, and inject the lens into the eye.

The injector tip 50 is a unitary elongated tubular member molded from a suitable plastic material, such as clear polyethalene, and comprises from its distal end a tip portion 54, a lens holder or "canoe" portion 56, and tubular support portion 58. The tip portion 54 has a cylindrical inner wall 55, and includes axially extending slots 60 as seen in FIGS. 3a–6a, and FIG. 3c. In addition, this tip portion tapers as seen in these Figures to a relatively thin end 61 at the extreme distal end. This construction provides a relatively flexible tip 54, particularly toward and at the distal end 61, which enables the intra-ocular lens to gently expand as the lens is controllably pushed through and out of the end of the tip 54. An example of dimensions of the tip 54 for exemplary purposes are an inner diameter of 0.105 inch for the tip portion 54, an outer diameter of 0.119 inch at the extreme distal end 61, an outer diameter of 0.158 inch at proximal end 62 of the tip 54, a length (L) of 0.530 inch, and a slot 60 length of 0.195 inch.

A flange 63 at the proximal end 62 of the tip 54 provides a forward stop for the constricting sleeve 51. The sleeve 51 is movable along the support portion 58 toward the stop 63 and over the holder 56 to curl an intra-ocular lens 66 placed in an opening 67. The opening 67 (note also FIG. 3f) is formed as a result of a longitudinal cut, which forms edges 68 and 69, and traverse cuts 72 and 73 in the holder or "canoe" portion 56. A cover (not shown) can be provided to snap over the IOL in the holder 56 after loading of the IOL and before curling thereof. A cover of this nature is disclosed in Ser. No. 07/106,044.

Briefly, the intra-ocular lens 66 is placed in the opening 67 in the holder or "canoe" portion 56 which has sides or side walls 64 and 65, and then the constricting sleeve 51 is moved toward the distal end of the cartridge 50 (to the left as viewed in FIGS. 3a, 4a, 5a and 6a) to encompass the holder 56 and also engage ad push in the side walls 64 and 65 to thereby progressively close the "canoe" section 5 and cnnsequently curl the lens 66 within the canoe section. It should be noted that the "canoe" section has no hinge of any type and preferably is of consistent thickness (essentially the same as the tube section 74 and tip 54) and thus the walls of the "canoe" can be curled to a cylindrical shape in an even fashion in curling the lens without any folding type operation.

Subsequently, the plunger 52 is advanced by the flexible cable 32 (not seen in FIG. 3a but note FIG. 8) to push the lens 66 out of the tip 54, whereby the lens can gently exit the relatively thin (at and near 61) and slotted (60) end of the tip 54 in a gentle manner.

Figures 3A, 3B, 3C, 3D, 3E, 4A, 4B, 5A, 5B, 6A, 6B:
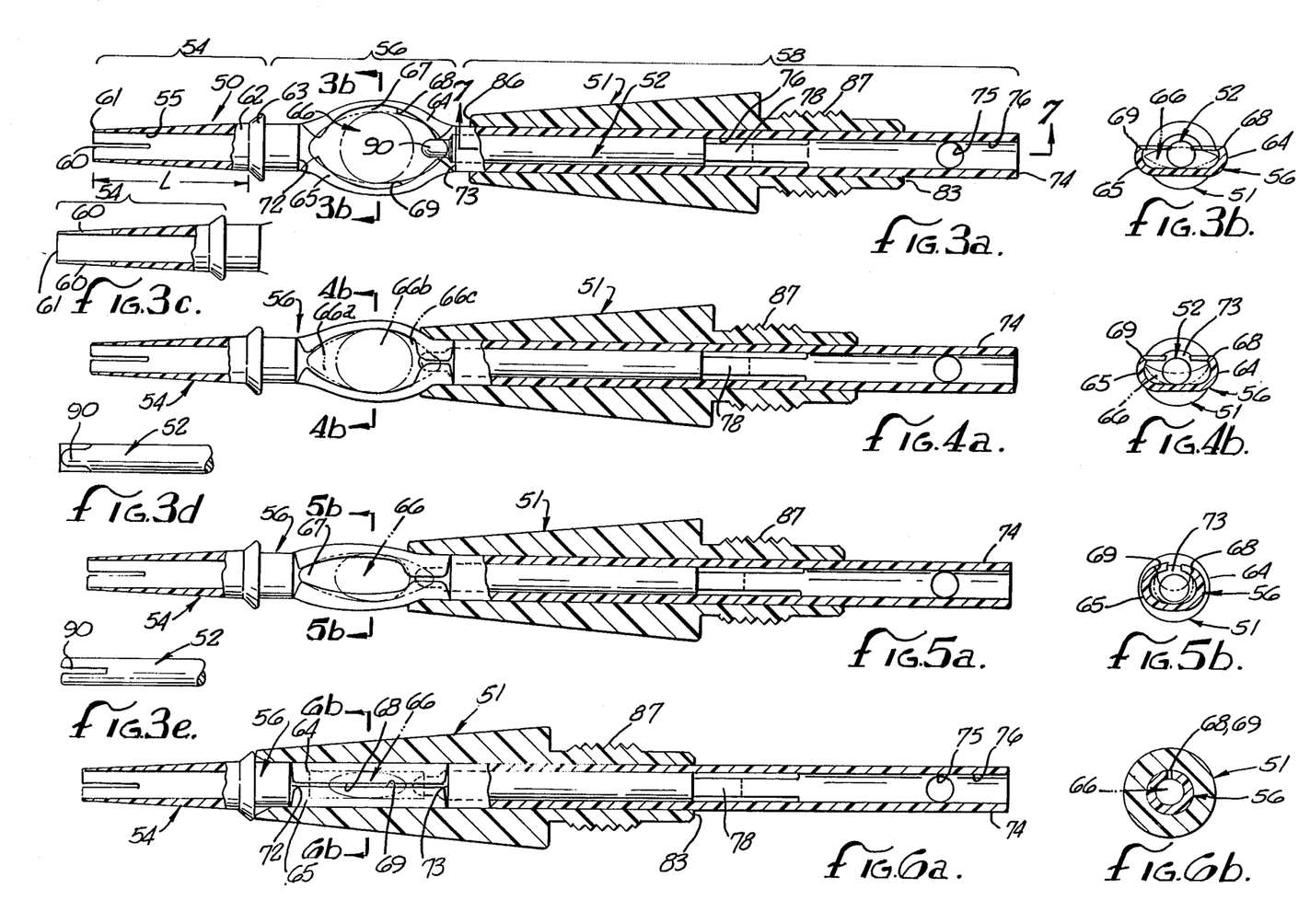

Continuing with a discussion of the structure of the insertion cartridge 12, the proximal support section 58 of the insertion tip 50 is in the form of a cylindrical tube 74 on which the constricting sleeve 51 is disposed for sliding axial movement (primarily to the left as viewed in FIG. 3a). In fact, the entire insertion tip 50 comprising the tip 54, holder 56 and support 58 preferably are one molded integral unit of essentially constant thickness, except for the end of tip 54 and the ring 63. The tube 74 includes a hole 75 in the proximal end which allows the injector tip 50 of the insertion cartridge 12 to be attached and firmly held in a lens cartridge loader (FIG. 12 to be discussed subsequently) as the sleeve 51 is moved to thereby cause the lens to curl in the holder 56. The tube 74 has an internal bore 76 for slidably receiving the plunger 52 and this bore continues on to the distal end 60. Additionally, the tube 74 includes a pair of arms 78 and 79 (both shown in FIG. 7, but only arm 78 being seen in FIG. 3a) in its wall on opposite sides of the tube and which have respective large ends forming tabs 80 and 81 which extend outwardly from the wall or surface of the tube 74 as the sleeve 51 passes (to the left) to engage the rear or proximal end 83 of the sleeve 51 to thereby lock the sleeve 51 between the tabs 80–81 and the stop 63 in the position as seen in FIG. 6a once the lens 66 has been fully curled. This locking action keeps the sleeve 51 from being retracted once the lens 66 is fully curled, and also ensures that the plunger 52 will push the lens out of the tip 54 without the support section 58 needing to be separately fixed to the instrument 11 since the sleeve 51 is threaded into the instrument as described below. Also, the tabs 80–81 are held into the bore 76 by the sleeve 51 until the sleeve reaches the position of FIG. 6a to perform the function of preventing the plunger 52 from being pushed backwards (to the right in FIG. 3a) such as during insertion of the IOL 66 into the cavity 67 of the holder 56 and into a slotted end 90 of the plunger.

The constricting sleeve 51 is essentially conical in shape and has a flared or chamfered forward or distal end 86 to engage the holder or "canoe" portion 56 and compress the walls of that portion to curl the lens 66. The proximal end of the sleeve 51 is threaded at 87 for mating with internal threads 88 (note FIG. 8) of the pen assembly 11 once the lens is loaded and the sleeve 51 is moved to the position shown in FIG. 6a and then threaded onto the instrument 11.

Figures 6C, 7, 8:
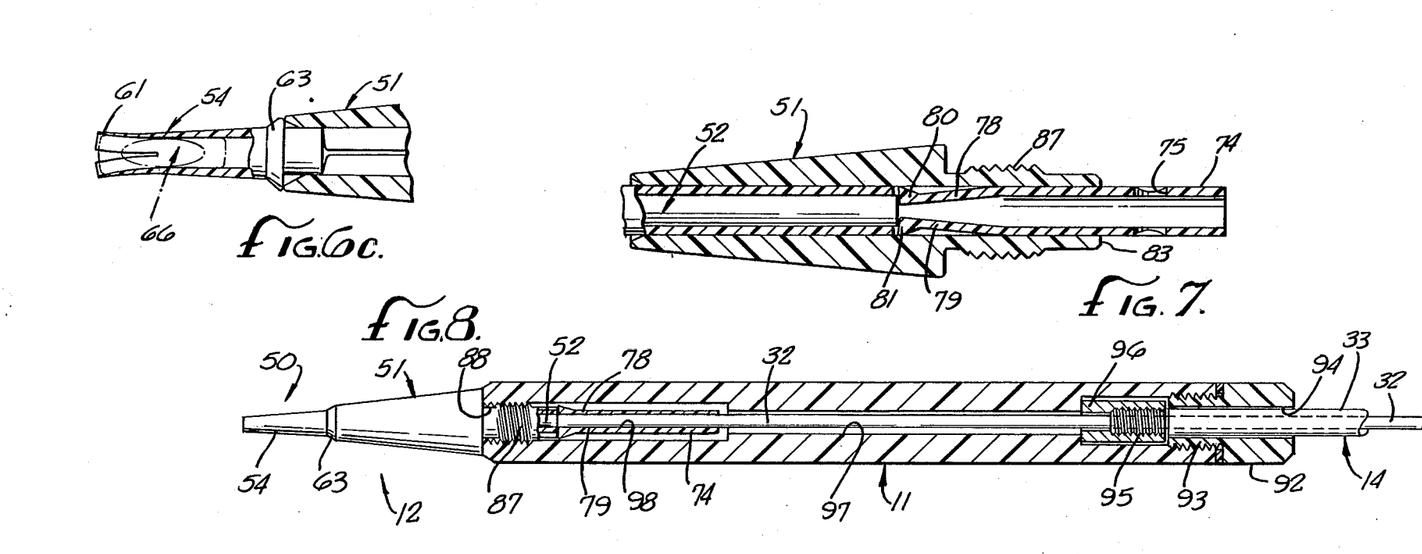
FIG. 6c is a partial view similar to FIG. 6a but showing the IOL partially ejected from the tip of the injector cartridge.
FIG. 7 is a partial cross-sectional view similar to FIG. 3a but rotated ninety degrees to show locking arms used in the injector tip.
FIG. 8 is a partial cross-sectional view of the hand held instrument with the flexible drive cable attached at the right end and the insertion cartridge attached at the left end ready for commencement of the lens insertion procedure.

The plunger 52 preferably is a solid cylinder, but has a slotted distal end 90 (note FIG. 3a, 3d and 3e) which partially straddles the proximal end of the intra-ocular lens 66 (note FIG. 3a). The plunger, as noted earlier is advanced by the cable 32 of the cable assembly 14. As best seen in FIG. 8, the flexible cable assembly 14 is secured in the proximal end of the instrument 11 by a retaining cap 92 which is threaded into the instrument at 93. The sheath or conduit 33 of the cable assembly 14 extends through a cylindrical opening 94 in the cap 92 and is secured at 95 in a cable collar 96 disposed in and forming a bushing within the end of the instrument 11. This structural arrangement provides a swivel end for the proximal end of the instrument 11 so that the instrument 11 can be conveniently grasped and rotated as needed by the physician without kinking of the cable assembly 14. The cable 32 extends into a bore 97 of the instrument and into the bore 76 in the proximal section 58 of the injector tip 50 of the cartridge 12. The cable 32 is secured to a drive shaft 98, the distal end of which abuts against the proximal end of the plunger 52 to push the plunger (to the left as viewed in FIG. 8 and FIG. 6a) to move the intra-ocular lens 66 out of the tip portion 54 of the injector tip 50.

FIGS. 3 through 6 illustrate in detail how the lens holder or "canoe" portion 56 of the injector tip 50 progressively closed or is changed to curl and confine the normally flat intra-ocular lens 66 essentially into a cylinder as the constricting sleeve 51 is moved to a closed position (to the left as seen in FIG. 3a). The intra-ocular lens 66 shown in these FIGS. is of the conventional solid body type IOL, and the same is inserted into the opening 67 formed by the curved sides of the wall of the holder portion 56 forms as a result of the aforementioned longitudinal cut which forms edges 68-69 and the transverse cuts 72 and 73 thereby creating the "canoe" shape as seen particularly in FIGS. 3a-3b, 4a-4b and 5a-5b. The IOL 66 is placed in the hole or cavity 67 in the "canoe" and the sleeve 51 is slid from the original position as seen in FIGS. 3a-3b progressively as shown in FIGS. 4a-4b, FIGS. 5a-5b, and finally to the closed position shown in FIGS. 6a-6b. The flared end 86 of the sleeve 51 engages the outer curved sides 64 and 65 and this end 86 and the cylindrical bore 85 in the sleeve 51 thereby pull these sides 64 and 65 together thereby closing the "canoe" into a cylinder. This action results in the inside surface of the "canoe" sides curling and returning to a cylindrical shape thereby compressing the IOL 66 progressively as seen in FIGS. 4 through 6 to curl the lens, finally reaching the fully curled or fully confined condition as shown in FIGS. 6a and 6b. This operation of sliding the sleeve 51 can be performed by hand by grasping and sliding the sleeve 51 but preferably is performed by the cartridge loader of FIG. 12 which will be discussed in detail subsequently.

Once the intra-ocular lens 66 has been curled as seen in FIGS. 6a-6b, the same is ready for insertion into the eye. The surgeon has made a small incision (such as 0.2 inch) in the eye in a conventional manner and has removed the clouded natural lens. The insertion cartridge 12 is threaded onto the hand held instrument 11 as shown in FIGS. 1 and 8. The control unit, via the foot control 25 may be operated to partially advance the intra-ocular lens 66 toward the tip 54 as may be desired by the physician. The physician preferably will advance the cable 32 slightly to ensure that the proximal end of the plunger 52 is engaged by the end of the cable 32, and then the distance display 17 will be manually reset to zero by depression of the reset button 21. Then, the insertion tip 54 is inserted into the incision in the eye, and the intra-ocular lens 66 is slowly advanced from its position as seen in FIG. 6a out of the tip 54 by the physician under control of the control unit 10 and foot pedal 25. Preferably, the advancement of the lens 66 follows a curve like that shown in FIG.11, and this can be accomplished by the physician operating the foot pedal 25 in conjunction with manual settings of the speed control 19. Alternatively, and preferably, a control system of the type shown in FIG. 10 is employed which automatically provides the lens advancing curve as shown in FIG. 11.

Figure 9:
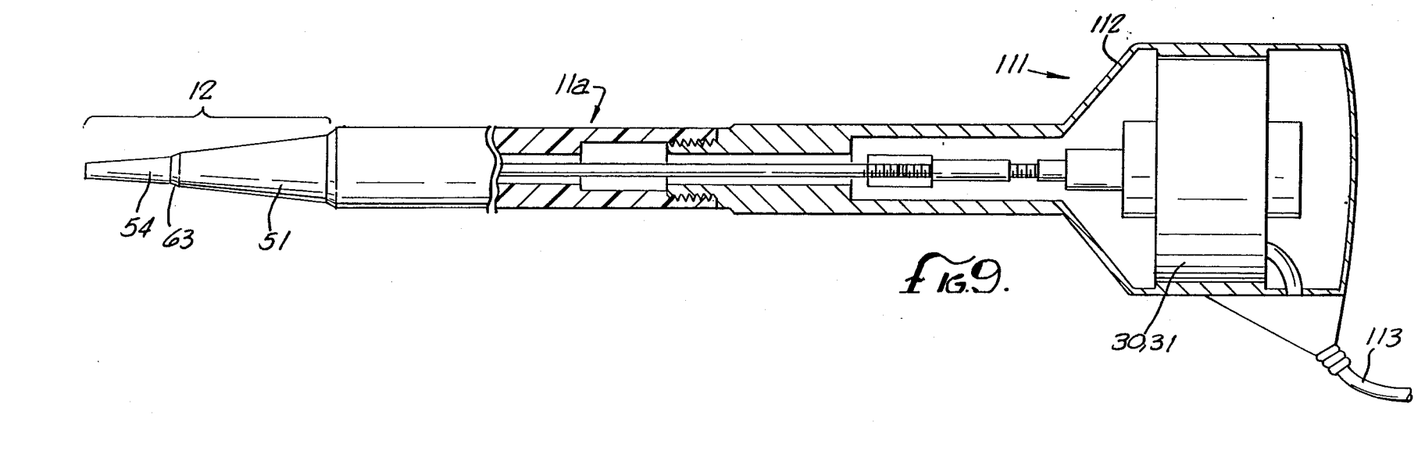
FIG. 9 is simplified cross-sectional view of an alternative hand held pusher pen wherein a compact linear motor actuator is included within the hand held instrument itself rather than in the control unit.

The rate diagram of FIG. 11 shows a preferred advancement sequence. In this diagram, position 1 indicates the drive shaft 32 having engaged the proximal end of the plunger 52. Position 2 indicates the plunger exerting pressure on the IOL 66. Position 3 indicates the IOL having moved into the barrel 55 of the injector tip 54, and at this point the injector tip 54 is inserted into the incision in the eye. Also at this point, the distance display 17 may be reset to zero if desired by depression of the reset button 21 on the control unit 10 of FIG. 1. At position 4 as seen in FIG. 11, the forward haptic 66a of the lens 66 starts emerging from the tip 61 of the injector tip 54 (note FIG. 6c). In position 5, the optic section 66b of the IOL starts emerging from the tip 61, and in position 6 the rear haptic 66c exits the tip. The physician can then remove the tip 54 from the eye and the IOL can be oriented in the eye in a conventional manner FIG. 9 illustrates an alternative form of the instrument 11, identified as 11a, and wherein the proximal end 111 includes a housing.112 containing the stepper motor 30 and linear actuator system. The motor system 30 is connected by an electrical cable 113 to the control unit 10 of FIG. 1. The only difference in the instrument of FIG. 9 is that the stepper motor actuator system preferably is smaller and forms an integral part of the hand held instrument 11a, and does not require the interconnecting flexible cable assembly 14 of the previously described embodiment.

Figure 10:
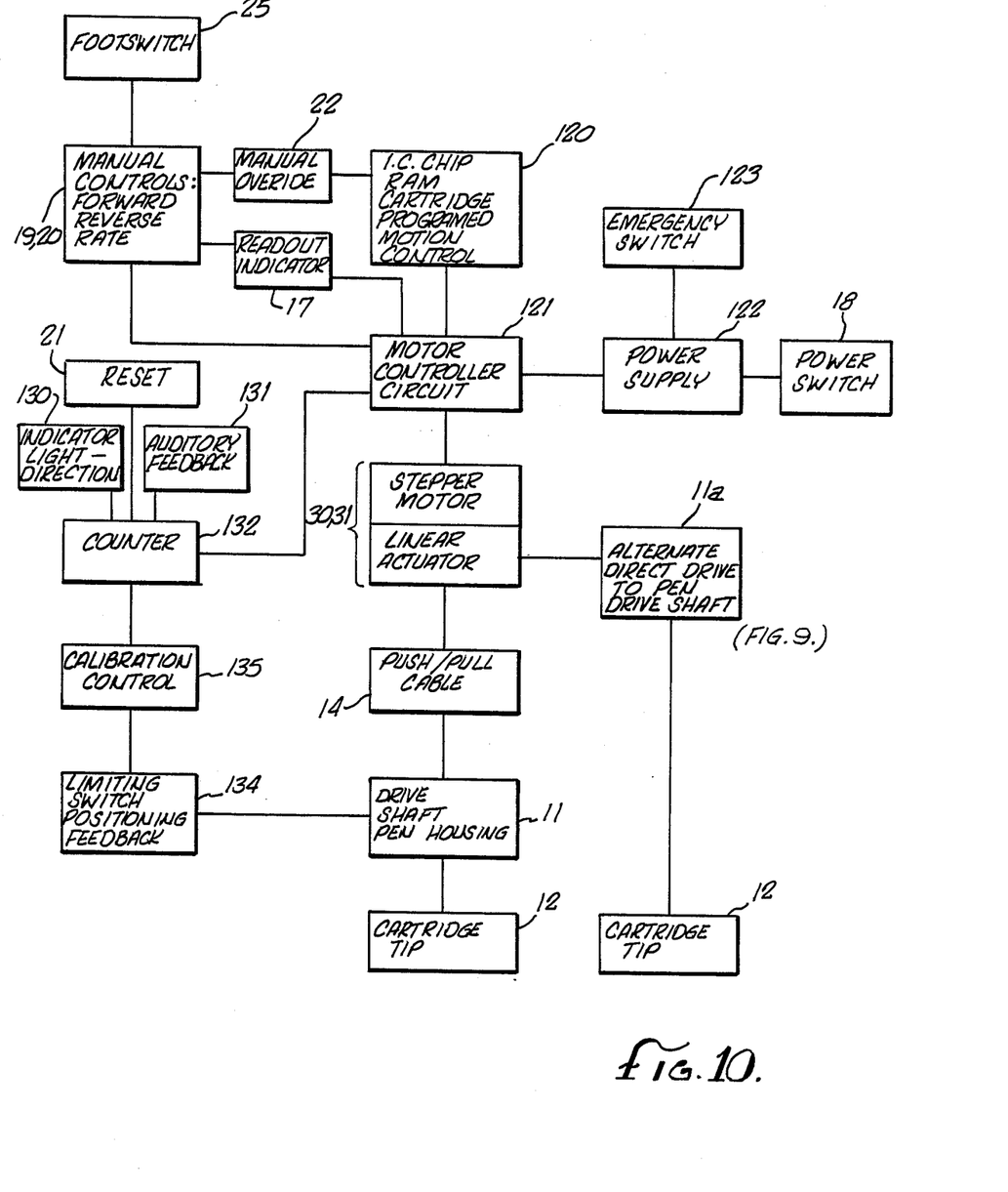
FIG. 10 is an electrical block diagram illustrating the electronic control components of the control unit of FIG. 1.

FIG. 10 is a block diagram of the overall electrical system for allowing manual and automatic control of advancement of the plunger and consequently advancement of the intra-ocular lens. The drive for the flexible cable 32 of the cable assembly 14 is the stepper motor driven linear actuator 30. Preferably, the shaft of the actuator 30 is directly attached to the cable 32 as earlier shown and discussed in connection with FIG. 2. As noted in connection with the discussion of FIG. 9, a smaller linear actuator may be housed in the instrument 11a, similar to an electric eraser.

As will be readily apparent to those skilled in the art, a fine and highly controlled motion is essential to the safe methodical delivery of the IOL. It is desired that the rate of movement or advancement of the plunger vary over the delivery cycle as previously discussed in connection with FIG. 11. Careful motion control is especially important when the plunger 52 first encounters the IOL 66 and when the IOL 66 emerges from the tip 54 into the eye. The combination of manual controls, programmed controls and foot switch control can provide the physician with accurate control down to 0.0005 inch per second. The direction and rate of the actuator may be controlled with the switch 20 and potentiometer 19 on the console of the control unit 10 discussed earlier.

In operation, the actual triggering of the actuator for movement of the plunger is achieved by depressing the foot switch 25. The system may be arranged so that the foot switch will also control rate like an accelerator pedal, and the surgeon can have the option to determine whether the foot switch includes rate control in addition to its on/off switching functions to advance the plunger. A suitable IC RAM chip 120 for providing programmed motor control (such as is indicated in FIG. 11) is provided in the control system to provide control of a motor control circuit 121 which controls the stepper motor and linear actuator 30. A power supply 122 is provided which is turned on and off with the on/off power switch 18 on the front panel of the control unit 10, and an emergency on/off switch 123 can be provided if desired. The foot switch 25, speed potentiometer 19 and forward/reverse switch 20 are connected, along with a manual override/automatic switch 22 and readout indicator 17, with the RAM chip 120 and the motor control circuit 121 to control the direction and speed of the actuator 30, as well as enable control of the same manually or automatically as previously discussed. In an automatic mode as selected by the switch 22, the foot switch 25 can operate merely to turn on and off the automatic rate control of the nature shown in FIG. 11. Additionally, a program delivery sequence of the type shown in FIG. 11 can be provided for each different type intra-ocular lens. Throughout the delivery of the lens, the digital display 17 can indicate the distance travelled, and direction and rate indicators can be provided if desired, such as a direction indicator 130. Auditory feedback can be provided as indicated at 131 to signal or alert the doctor at key points of the delivery cycle. A counter 132 is provided to keep track of the movement and direction. Additionally, and if desired, suitable feedback can be provided from the instrument 11 by positioning feedback circuit 134 and through calibration control 135 in a conventional closed loop servo control fashion.

FIGS. 12a through 12f illustrate an intra-ocular lens cartridge loader according to the present invention for enabling the intra-ocular lens 66 to be loaded into the insertion cartridge 12 in a simple manner and by using only on hand. This loader includes a base 140 which may be clamped to a table 141 or the like by a suitable clamp 142. The base includes upstanding internal brackets 146 and 147 for receiving and holding the injector cartridge 12. The bracket 146 includes a pair of fingers 148 and 149 for supporting the injector tip 54 of the cartridge 12. The bracket 147 includes an upstanding pin 150 which extends into the opening 75 in the proximal end of the tubular support section 58 of the injector cartridge 12.

Figure 12A:
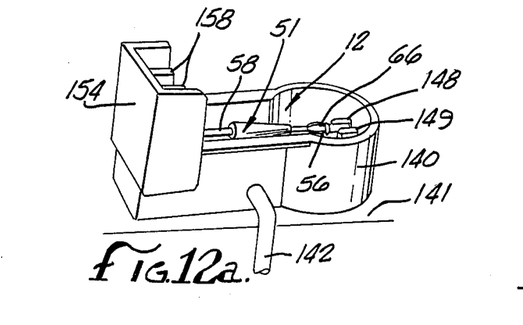
FIGS. 12a through 12f are perspective and cross-sectional views of an intra-ocular lens cartridge loader for enabling an intra-ocular lens to be loaded into the insertion cartridge in a simple on hand operation.
Figure 12B:
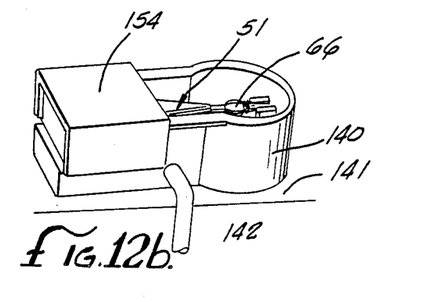
Figure 12C:
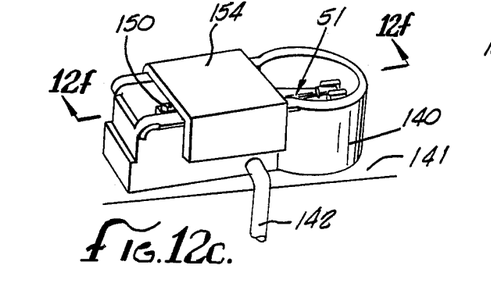
Figure 12D:
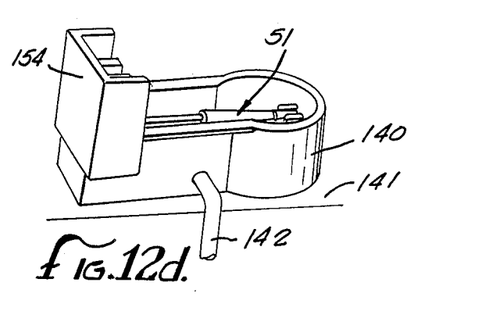
Figure 12E:
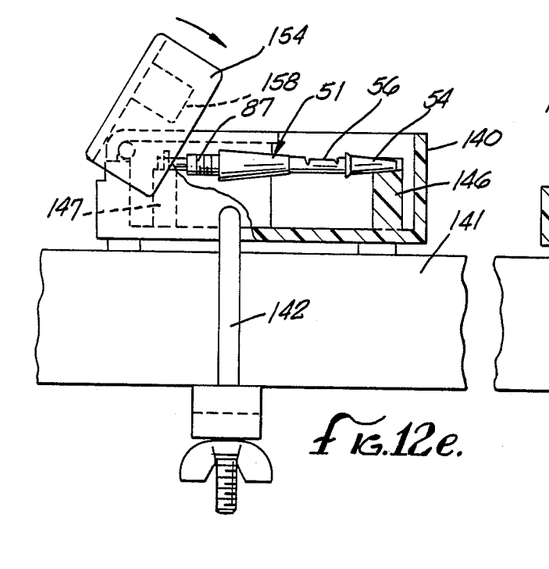
Figure 12F:
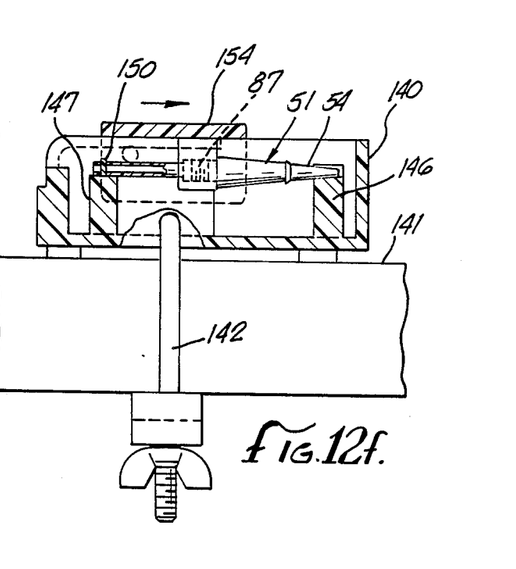

An actuator 154 is hinged and slidably supported on the base 140 so that the actuator 154 can be pivoted upwardly out of the way as shown in FIGS. 12a and 12e to allow insertion of the cartridge 12 into the loader. Additionally, the actuator 154 can be pivoted downwardly as seen in FIGS. 12b, 12c and 12f, and then grasped and slid forward along flanges as seen in FIGS. 12c and 12f to move the constricting sleeve 51 to the stop provided by the ring 63 to thereby curl and compress the intra-ocular lens in the manner described previously. The actuator 154 includes an inverted "U" shaped bracket 158 which loosely straddles the threads 87 of the proximal end of the constricting sleeve 51 to grasp the same for movement to the position indicated in FIGS. 12c and 12f. Internal pins 159 on both inside walls of the actuator 154 engage and ride on the underside of flanges 155 and 156 to allow the actuator 154 to be pivoted as shown in FIGS. 12a, b, d and 3, and to be slid as seen in FIGS. 12b, c and f. It will be apparent that the cartridge 12 can be readily inserted into the loader of FIG. 12 by one hand when the actuator is opened as seen in FIG. 12a, the actuator 54 pivoted downwardly (FIGS. 12b and 12e) and then the actuator 154 moved (FIGS. 12c and 12b) with one hand to slide the sleeve 51 and curl the lens. The actuator then is slid back (to the left in FIGS. 12) and pivoted up (FIG. 12d) to allow removal of the now loaded cartridge 12.

As examples of materials and dimensions, in addition to those previously given with respect to the tip 54, the overall insertion tip 50 of the insertion cartridge 12 may have a length of 2.94 inches from the extreme distal tip 61 to the center line of the proximal hole 75, and a nominal outside diameter of 0.158 inch. The locking arms 78 and 79 may have a length of 0.363 inch and a width slightly smaller than the inside diameter (0.105 inch) of the bore 76. The ring 63 may have an axial length of approximately 0.05 inch and a diameter of approximately 0.24 inch. The length of the entire tip 54 from the proximal stop of ring 63 thus is 0.580 inch. The longitudinal slit in the lens holder 56 forming the edges 68 and 69 may have a length of approximately 0.545 inch, and the transverse slits 72 and 73 extend from side to side and therefore have a linear length of approximately 0.158 inch and a depth of approximately ½ the diameter or 0.079 inch.

Figure 3F:
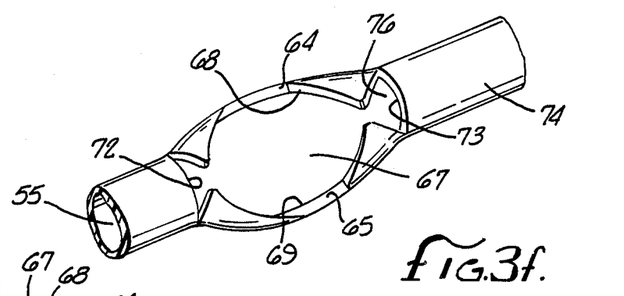
FIG. 3f is a perspective view of the "canoe" lens holder of FIG. 3a, and FIGS. 3g and 3h are further detailed plan and cross sectional views thereof.
Figure 3G:
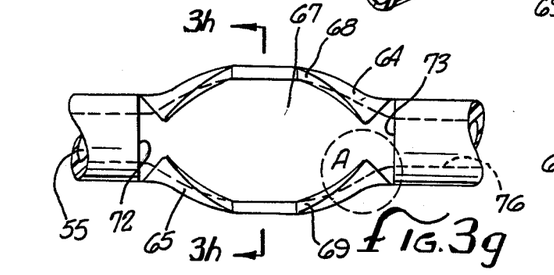
Figure 3H:
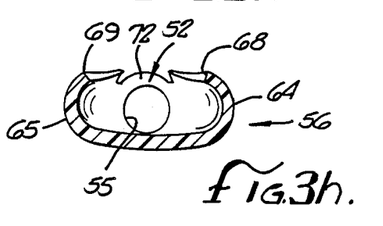

The "Canoe" shape tip as particularly seen in FIGS. 3(f)–3(h) is molded in the open configuration as shown. The flared open area 67 forming the lens holder is produced by a plug (not shown) that interrupts the otherwise continuous lumen 76 formed by coring pins. In the demolding process, the plug is pulled out of the "Canoe" (up from the Canoe as seen in FIG. 3(g)) while the pins are extracted from the front and back (from the left and right as seen in FIG. 3(g). Any undercut area such as area "A," where material is partially molded over the plug do not present a problem in removal of the plug because of the flexibility of the material (e.g., polyethalene) used.

The sleeve 51 preferably is molded from clear polyethalene and has an overall length of 1.483 inch (including the threaded proximal end) and the conical section thereof a length of 1.0 inch. The outer diameter of the distal end of the cone may be 0.24 inch and the outer diameter of the proximal end 0.44 inch. The inside diameter is 0.16 inch. The plunger 52 may be molded from pigmented polyethalene, and have a length of 0.9 inch and a diameter of 0.103 inch. The slot 90 therein may be 0.015 inch wide, and 0.19 inch long for receiving a typical solid body type IOL.

The stepper motor 30 may be an Airpax model K92211-P2 or equivalent twelve volt unit. It may be driven directly from a Signetics SAA1024 controller chip. The motor speed may be controlled through a variable frequency oscillator and scaler which can be activated by the foot control switch. Preferably, the stepper position is displayed in 0.001 inch increments on a three digit seven segment display of conventional design. The position indicated is relative since the display may be reset as previously explained to zero at any time and then the display value will represent positive or negative steps from the last reset position. The normal operation allows the physician to select the direction, reset the display to zero and then increment the position in 0.001 inch increments as long as the foot switch is depressed. A typical full range is 0.875 inch equaling a count of 875 on the display. The potentiometer control allows linear speed control of advancement, and preferably provides operation in a range from about five steps per second to one hundred fifteen steps per second which translates approximately to 0.75 inch in 150 seconds minimum speed or 0.75 inch in 6.5 seconds maximum speed.

While embodiments of the present invention have been shown and described, various modifications may be made without departing from the spirit and scope of the present invention, and all such modifications and equivalents are intended to be covered.

What is claimed is:

1. Apparatus for inserting a flexible lens into an eye through an incision in the eye comprising
   lens holder means for receiving and holding a flexible lens, said holder means including a holder having substantially a "canoe" shape when the holder is in an opened condition thereof in which the lens can be placed when the lens is in a normal flat state, the holder being formed by a molded tubular section of plastic material having an open top and outwardly extending sides formed as a result of at least one elongated slit type opening, and said holder sides being compressed to essentially the form of a closed hollow cylinder with a cylindrical inner surface when in a closed condition to curl the lens into a generally confined tubular shape, tip means integrally formed with said lens holder means and including a cylindrical bore mating with and forming a continuation of the inner cylindrical surface of said lens holder means, said bore extending from a proximal end of said tip means to a distal end thereof, and said tip means having a substantially cylindrical wall of decreased thickness toward the distal end thereof and includes at least one slot therein near the distal end whereby the distal end of said tip means is more flexible than the proximal end thereof for allowing the curled lens to pass through said tip means and to gently expand as the lens nears and exits the distal end of said tip means, sleeve means for slidably engaging said holder means and moving the sides of the holder means together for curling said lens, and advancing means for moving said lens from said holder means to and through said tip means for causing ejection of the lens from said insertion cartridge.

2. Apparatus as in claim 1 further including
instrument means constructed to be hand held by a surgeon, said instrument means having a first end for receiving flexible actuator means for engaging with said advancing means, and having a second end for connection with said sleeve means, and control system means including linear actuator means coupled with said flexible actuator means for enabling controllable advancement of said advancing means in small increments.

3. Apparatus as in claim 2 wherein
said sleeve means includes means at its proximal end for attaching the same to said second end of said instrument means.

4. Apparatus as in claim 1 wherein said tip means has a diameter of less than approximately two tenths inch.

5. Apparatus as in claim 1 wherein
said holder means has extended from the proximal end thereof tubular means for containing said advancing means and for supporting said sleeve means for slidable movement along said tubular means to close said holder means in curling the lens, said tubular means including locking means normally maintained in a first position by said sleeve means but which is allowed to move to a second position upon sliding movement of said sleeve means with respect to said tube means in a forward direction to lock and prevent sliding movement of the sleeve means in a direction opposite the said forward direction.

6. Apparatus as in claim 4 including
ring means integrally formed thereon between the holder means and tip means, said ring means providing a limiting stop for said sleeve means in movement thereof in the forward direction, said locking means locking said sleeve means against the stop when said sleeve means is moved in the forward direction to engage the stop.

* * * * *